United States Patent [19]

Dietrichs et al.

[11] 4,181,796

[45] Jan. 1, 1980

[54] PROCESS FOR OBTAINING XYLAN AND FIBRIN FROM VEGETABLE RAW MATERIAL CONTAINING XYLAN

[75] Inventors: Hans-Hermann Dietrichs, Reinbek; Michael Sinner, Dassendorf; Fritz Opderbeck, Munich; Karl-Heinz Brachthauser, Ratingen, all of Fed. Rep. of Germany

[73] Assignee: Projektierung Chemische Verfahrenstechnik Gesellschaft mit beschrankter Haftung, Dusseldorf, Fed. Rep. of Germany

[21] Appl. No.: 816,464

[22] Filed: Jul. 18, 1977

[30] Foreign Application Priority Data

Jul. 20, 1976 [AT] Austria .................................. 5346/76

[51] Int. Cl.² .......................... C07H 1/06; C07H 1/08
[52] U.S. Cl. .................................... 536/1; 127/46 R; 536/115; 536/119; 568/863

[58] Field of Search .................. 536/1, 115, 119, 635; 260/635; 127/46; 195/33

[56] References Cited

U.S. PATENT DOCUMENTS

| 2,073,616 | 3/1937 | Acree | 536/1 |
| 3,248,382 | 4/1966 | Marchessault et al. | 536/119 |
| 3,687,807 | 8/1972 | Johannessen | 536/1 |
| 3,780,017 | 12/1973 | Spalt et al. | 536/1 |
| 4,017,642 | 4/1977 | Orth, Jr. et al. | 536/1 |

FOREIGN PATENT DOCUMENTS

9352 of 1913 United Kingdom ....................... 536/1

*Primary Examiner*—Johnnie R. Brown
*Attorney, Agent, or Firm*—Donald D. Jeffery

[57] ABSTRACT

A process for the production of xylan and fibrinous material from vegetable raw material by treating the raw material with saturated steam at a temperature of from 160° to 230° C. for a period from 2 minutes to 4 hours.

10 Claims, 3 Drawing Figures

PROCESS FOR OBTAINING XYLAN AND FIBRIN FROM VEGETABLE RAW MATERIAL CONTAINING XYLAN

The present invention relates to a process for obtaining xylan and fibrin from vegetable raw materials containing xylan which can be decomposed by treatment with steam under pressure.

It is known that cellulose-containing raw materials can be decomposed in order to obtain and work up products contained in the raw material, particularly in wood. According to the nature of the desired products, various methods of decomposition are used. In general, these are decomposition processes using chemicals, under the influence of which the cell wall bonds are loosened or cementing substances are dissolved, so that the fibrous structure of the cellulose fraction can be exposed by defibrination and supplied for use in this form as raw material for, for example, boards, paper. According to the conditions of decomposition, the substances associated with the cellulose are removed, so that pure cellulose is available for further processing to artificial silk, artificial wool, etc. The separated associated substances are produced in dissolved form and are destroyed.

It is further known that raw materials, e.g. ground wood, may be subjected to steam or steam pressure treatment to make possible or to facilitate, by loosening the cell wall bonds, subsequent defibrination. The aim of this process is essentially to expose the fibrous structure of the cellulose fraction and to supply it in this form for use, e.g. in the manufacture of fibre boards or as fodder (CN patent spec. No. 933 028). Separated associated substances are produced in dissolved form and are mostly destroyed.

The purpose of the present invention, however, is to process xylan-containing vegetable raw materials in such a way that to the greatest possible extent all substances contained in the raw material are utilised. In particular it is intended that xylan should be separated in high yield and possibly subjected to further treatment.

According to the present invention there is provided a process for the production of xylan and fibrinous material from xylan-containing vegetable raw materials which can be disintegrated by steam pressure treatment and defibration, which process comprises treating the raw materials with saturated steam at a temperature of from 160° to 230° C. for a period from 2 minutes to 4 hours, the vegetable raw material disintegrated in this way being lixiviated with an aqueous solution, and wherein xylans and xylan fragments are separated from the solution in purified form from monosaccharides and any other impurities and, if desired, the xylan and xylan fragments, optionally still in solution, are hydrolysed to xylose which, if desired, may itself be reduced in known manner to xylitol.

Examples of raw materials are hardwoods, straw, bagasse, grain husks, corn-cob residues and maize straw. As vegetable raw material, those raw materials in particular are used which have a xylan content of for example more then about 15 wt.% preferably more than 25 wt.%. It is however expressly stated that according to the invention vegetable raw materials with a lower xylan content may also be used, especially when the utilisation of the fibrous residues obtained after lixiviation of decomposed vegetable raw material is of great economic interest. This again depends on what vegetable raw materials are available for processing in the particular geographic region.

As already stated above, pressure steam treatment and defibrination to disintegrate the cell bonds of vegetable raw materials is itself a known process. According to the invention, the treatment is carried out in such a way that chemical decomposition of the products contained in the raw material is prevented to the greatest possible extent. It is thus undesirable according to the invention to add acids, bases or other chemical substances in the steam pressure treatment. The steam pressure treatment should be as mild as possible in relation to the xylans and xylan fragments. Decomposition of the xylans to monosaccharides should therefore be avoided as far as possible.

To solve this problem, it has been found particularly advantageous to carry out the steam pressure treatment at temperatures above about 175° C., preferably above about 180° C., but below about 220° C., preferably below about 200° C., and particularly advantageously in the range of about 185° to 190° C. If the temperature chosen is too high, undesirable decomposition of the xylans to monosaccharides can occur. If the temperature is too low, the disintegration may be insufficient or take too long. To keep the disintegration as mild as possible, the duration of the steam treatment should be as short as possible. In general, the lower the temperature used the longer will be the duration of treatment.

The maximum duration of the steam treatment should preferably be about 60 minutes, more preferably about 15 minutes and particularly advantageously about 5 to 8 minutes. The lower limit for the duration of the treatment is essentially determined by the need to achieve adequate disintegration. The times cited refer to the duration of the action of steam at the temperatures quoted above on the starting material.

During the disintegration treatment acetyl groups are split off from the starting raw material, forming molecules of acetic acid. The acetic acid has a beneficial effect on the disintegration. In the case in which the vegetable raw material subjected to disintegration splits off very little acetic acid, it may be advantageous to add acetic acid or other acids, however, in general not more than about 6 wt.% acid, calculated on the dry raw material, should be present.

The vegetable raw material disintegrated in this way, after brief defibrination is lixiviated according to the invention with an aqueous solution. The lixiviation may be carried out in several stages.

According to a preferred means of operating the process of the invention, the lixiviation is carried out successively with water, optionally repeated several times, and with an aqueous alkali solution, likewise optionally repeated several times. It is particularly advantageous and economical to leach the still hot vegetable raw material with water immediately after the steam pressure treatment, since, even if cold water is used, this is heated by the hot raw material and naturally a larger proportion of the xylans dissolve. It is of course also possible to use previously heated water. In this way a substantial proportion of the xylans is already extracted with water. The extract solution can be separated from solid components by known processes, such as by filtration, centrifuging, decantation by suction etc. For this purpose, the equipment conventionally used for processing cellulose-containing raw material, for example vacuum cell filters, band presses, and batch centrifuges, may be utilised. The lixiviation can be carried out on the counter current principle.

For certain applications it may be appropriate not to carry out a further extraction, and this is particularly so when the starting material contains relatively little xylan and the objective is essentially to pass on the fibrous residues obtained after lixiviation to profitable applications.

However, it is particularly preferred to carry out after the extraction with water a further extraction step using a diluted base.

The base used for leaching is preferably an alkali, in particular caustic soda solution. This is cheap and moreover has a swelling effect on the vegetable raw material. Caustic potash may also be used, but is as a rule dearer. Caustic soda has the further advantage that it can subsequently easily be neutralised to form products which pose no problems in relation to environmental contamination. The concentration of bases in the extract solutions should be as small as possible since large amounts of base are undesirable in further processing. It is therefore preferable that the concentration of the base when NaOH is used should be not greater than about 2 wt.%, preferably not greater than about 1 wt.% and most preferably not more than about 0.6 wt.%, calculated on the weight of the extract solution. A suitable lower limit of concentration is about 0.1 wt.%, preferably above about 0.2 wt.% and most preferably above about 0.3 wt.%. If other bases are used, the corresponding optimum amounts can be determined by simple experiments.

It is also possible according to the invention to lixiviate immediately with an aqueous alkaline solution. In this case, however, the entire alkaline extract must usually be purified, which is not generally necessary, as will be shown below, when the lixiviation is carried out successively with water and an aqueous alkali solution according to the preferred method. With many vegetable raw materials very good results are obtained with immediate lixiviation with alkali solution by precipitating the xylan and xylan fragments from extract solutions.

If after lixiviation with water, lixiviation with aqueous alkali solution is carried out, the latter is produced as a rule in so pure a form that the separation of the xylan and xylan fragments in purified form from low molecular weight sugars is no longer necessary. The usual purification and decolourisation of the solutions by means of known processes of sugar processing technology can still be carried out, whereby this purification can sometimes be carried out when the xylan has been further processed to xylose by hydrolysis.

It is thus possible to proceed so that only xylans and xylan fragments from extract solutions obtained with water need to be separated in purified form essentially from monosaccharides and possibly other impurities.

The temperature at which the alkaline lixiviation is carried out has a strong influence on the yield of xylan. It has been found surprisingly that in this respect large differences exist between individual vegetable raw materials. The optimum lixiviation temperature depends moreover on the steam pressure disintegration conditions, on the concentration of the alkali solution and on the duration of the alkali treatment. In particular, at low disintegration temperatures lixiviation needs to be carried out for a longer time. The optimum lixiviation conditions can easily be determined experimentally on disintegrated vegetable raw materials.

It has been found that xylan and xylan fragments extracted from steam pressure disintegrated material with alkali at room temperature are astonishingly temperature stable. Thus, for example, xylans and xylan fragments in the alkali extracts from birch (room temperature) do not show a perceptible decrease in respect of their xylose content until the temperature in a subsequent 30 minute heating is above about 70°–80° C.

As expected, lower yields of xylans and xylan fragments were obtained when the disintegrated birch was washed with alkali at 100° C. It has been found, however, that at temperatures up to about 50° C. and alkali treatment durations of up to about 20 to 45 minutes the yields of xylans and xylan fragments lie in the region of the amounts achieved at room temperature.

Surprisingly, a quite different extraction however was found with other raw materials, such as wheat straw. The yield of xylans and xylan fragments increases sharply with the temperature and reaches a maximum in the range of 50° to 80° C. according to the raw material, degree of disintegration, duration of alkali treatment etc. The yield does not drop below that achievable at room temperature until about 70°–90° C.

The temperature of the alkali treatment also has a substantial influence on the purity of the xylans and xylan fragments in the extracts. With the majority of raw materials the proportion of non-carbohydrates, in particular phenolic substances, increases with the temperature. Usually these substances have no adverse effect on the degree of purity of the xylose, since in the subsequent acid hydrolysis of the xylans and xylan fragments they are precipitated and can easily be filtered off. Extraction at elevated temperature can however with certain raw materials increase the proportion of foreign sugars, which can make the production of pure xylose more difficult. Since strong differences exist between individual raw materials and their pretreatment, the optimum extraction conditions in respect of yield (see above) and purity of the xylans and xylan fragments must be determined for individual disintegrated fibrous materials. This can be done in a simple manner, as shown in the examples. With birch, extraction at the lowest possible temperature (not above 60° C. for 30 min. with 1% NaOH) and low NaOH concentration appears to be advantageous, since at higher temperatures the yield decreases and the proportion of hexoses increases. With wheat straw the lixiviation can advantageously be carried out at higher temperature, since the yield increases considerably with the temperature and the proportion of foreign sugars increases only slightly.

An essential step in the process according to the invention consists in separating the xylans and xylan fragments in the aqueous extracts from monosaccharides and other impurities. In this way a purified solution of xylans and xylan fragments is obtained in extremely high yield calculated on the xylan content of the vegetable raw material used. It is surprising and could not be predicted that in carrying out the process according to the invention it is possible on the one hand to obtain reactive fibrins of which the carbohydrates consist mainly of cellulose from the vegetable raw material and on the other hand to isolate the xylans and xylan fragments in high purity and yield which can then be further processed to xylose or xylitol. The separation of xylans and xylan fragments by the use of strongly basic ion exchange resins in the OH form, such as Lewatit MP 5080 (macroreticular) or Lewatit M 5080 (both from Merck AG) or Amberlite IRA 900 (macroreticular). According to the charge of such ion exchangers with the aqueous extracts, the monosaccharides can be eliminated by:

1. displacement by the xylan and xylan fragments
2. elution with weakly alkaline aqueous solutions
3. elution with weak acids (such as $H_2CO_3$)
4. elution with aqueous salt solutions of low concentration (such as Na $HCO_3$ or $Ha_2HPO_4$).

In process 1, the ion exchanger is charged to its maximum capacity to absorb xylans and xylan fragments (which, by reason of their acid side groups, are more strongly attached to the ion exchanger). The monosaccharides can be washed out with water. The charging of the ion exchanger is critical. If the capacity is exceeded, a breakthrough of xylan fragments occurs. If the exchanger is not sufficiently charged, the monosaccharides are not separated. By analysis of the outflowing solution the optimum degree of charging can be determined.

The concentration of alkali needed in process 2 depends on the charging of the ion exchanger and the composition of the xylan solution. If the concentration of the alkali is too low, the monosaccharides are not completely washed out. If the concentration is too high, xylan and xylan fragments are also washed out. The optimum concentration in each case can easily be determined by experiment. For the reasons given above, the preferred alkali is caustic soda. When caustic soda is used, concentrations of 0.1 to 0.4 wt.% are suitable. After separation of the monosaccharides the ion exchanger can be washed free from excess caustic soda with water without loss of xylan and xylan fragments.

In process 3 the acid should not be so strong that it elutes the xylans and xylan fragments together with the monosaccharides. The required concentration can be determined in an analogous manner to that described in process 2 for determining the optimum concentration of the alkali.

In process 4 the optimum concentration of the salt solutions is determined analogously.

After removal of the monosaccharides, the xylans and xylan fragments can be washed from the ion exchanger with either 1. acids (such as $H_3PO_4$, $HNO_3$; $H_2SO_4$ or HCl)
2. after hydrolysis in the ion exchanger bed with acids such as those in 1 in the form of monomeric and low oligomeric fassion products
3. solutions of basic salts (such as $Na_2CO_3$)
4. strong alkali solution.

Xylans and xylan fragments are easily soluble in alkaline media, but can be precipitated in acid media. Nevertheless, the use of acids for elution is particularly advantageous if further processing to xylose is envisaged. In this case the acid used for elution can serve at the same time to carry out the hydrolysis. To guard against the possibility that in elution with acid, xylans will be precipitated and therefore remain in the ion exchanger bed, the ion exchanger charged with xylan and xylan fragments can be heated after addition of acid to high temperatures of for example up to about 150° C., resulting in hydrolysis in the ion exchange bed. The upper temperature limit is determined essentially by the temperature stability of the ion exchanger. The ion exchangers named above have long-term temperature stability up to about 150° C. The monomeric sugars formed by hydrolysis, i.e. essentially xylose, can easily be washed out of the ion exchanger with water. It is of particular advantage that by the last process concentration of the solutions can be achieved.

If, with the use of certain raw materials, aqueous solutions exist which, in addition to xylan and xylan fragments, contain only small quantities of other sugars, of which the isolation is not profitable, purification from foreign substances and colouring matter can be effected by passing the extract solutions through the above-named ion exchange resins in the Cl form. With such treatment there is scarcely any loss of carbohydrates, in particular of xylan and xylan fragments, while colouring substances are very extensively removed.

The essential concept of the invention consists in that from the aqueous extracts the xylans and xylan fragments are isolated in pure form. This isolation has been described in detail above with the use of strongly basic anion exchange resins. The monosaccharides and other low molecular weight contaminants can also be supplied to yet another economic utilisation. For example the sugar fraction contained in the eluate can be used for the manufacture of protein or, after concentration, as a liquid cattle feed. Other purification processes may also be used for the isolation of the xylans and xylan fragments. Examples of such processes are ultrafiltration, dialysis, gel filtration and fractional precipitation. For lixiviation extracts the last is preferably carried out by making the alkali extracts weakly acid, whereby part of the xylan is precipitated and can be separated. To the solution an organic solvent can be added in which the xylan and the xylan fragments are insoluble or only slightly soluble, but which is a solvent for the monosaccharides or other unwanted contaminants. Xylan and xylan fragments are precipitated in this way in a very pure form. Particularly suitable solvents for this purpose are alcohols. Other solvents which possess the solvent properties defined above may also be used.

In most cases it is desired to work up the xylans and xylan fragments present as a mixture into xylose and perhaps further into xylitol. For this purpose the solutions obtained, which contain the xylan and xylan fragments in purified form, are hydrolysed directly, i.e. without special isolation of the xylans and xylan fragments contained in them, unless, as described below, the hydrolysis of the xylans and xylan fragments has already been carried out in the ion exchange bed. The hydrolytic processes are themselves known. It is however of particular advantage that the hydrolysis of the dissolved xylans and xylan fragments obtained by the process of the invention be carried out under milder conditions, e.g. by the use of smaller amounts of concentrated acid, than the hydrolysis of the xylans in the cell wall bonds of the vegetable raw material, i.e. hydrolysis of for example wood or straw.

It is also particularly advantageous that the xylans and xylan fragments present in the dissolved form, unlike the xylans present in the cell wall bonds of the raw material, be converted by xylanolytic enzymes both in the free state and also particularly advantageously in carrier-combined form in very high yields into xylose in addition to the 4-O-methylglycuronic acid found in small amounts in the xylans.

When it is desired to prepare xylitol from the xylose it is expedient to purify the hydrolysate first over anion exchanger. On the ion exchanger both the 4-O-methylglycuronic acid and the acid used in the acid hydrolysis are fixed, while xylose can pass freely through the ion exchange column (cf. K. Dorfner; Ionenaustauscher (ion exchangers), Verlag Walter de Fruyter & Co. Berlin 1970, p. 207, M. Sinner, H. H. Dietrichs and M. H. Simatupang, Holzforschung, 26 (1972) 218–228).

From the xylose solution purified in this way the xylose can be isolated in a known way if it is required as such. The 4-O-methylglycuronic acid is easily removed together with the acid used for the hydrolysis. Other sugars contained in the solution, in particular glucose, are easily removed by recrystallisation, since they are present in only small amounts.

A primary objective of the process according to the invention consists, however, in that the purified xylose obtained by the above process is further worked up by preferential catalytic hydrogenation in a known manner to xylitol (cf. DT-OS Nos. 25 36 416 and 24 18 800, DT-AS 20 05 851 and 10 66 567, DT-PS 5 809 804 and FR-PS 2 047 193). With this way of carrying out the process, xylitol is thus prepared in a highly pure state in a simple manner by an economical process from vegetable raw materials with a high xylan content (cf. DT-AS No. 1 066 568). The xylose can also be degraded to furfurol. For this purpose it is not necessary that the xylose should first be separated in a pure form. As with the other further processing methods described above, the purified xylose solution can be directly converted into furfurol in a known manner, for example by the action of strong acids. The conversion into xylitol can also be carried out microbiologically (cf. DT-PS No. 19 39 035).

The residue obtained after lixiviation of the disintegrated vegetable raw material represents a valuable fibrinous product. This fibrinous product can be used for the manufacture of various valuable products. One sphere of application is the manufacture of fibre boards and cardboard. A special advantage in this case is that no effluent problems are involved in the manufacture of fibre boards and cardboard, since the fibrinous product obtained by the process of the invention is already free from unwanted ingredients. A further advantage is that in the manufacture of fibre boards only a small amount of paraffin wax can be added in a known way, while the addition of any other chemicals is unnecessary. The manufactured boards have very advantageous properties. It may be expedient to subject the fibrinous product obtained according to the invention to grinding in the refiner before further processing into fibre board, in order to achieve the requisite degree of fineness for fibre board.

Another particularly advantageous field of application for the fibrinous product lies in its use as fodder. In this case, of course, the residue must not contain large quantities of bases which would be harmful in its use as fodder. In the lixiviation of the disintegrated raw material is done with alkaline solution, the residue must therefore be thoroughly washed with water in order to obtain a suitably clean product as fodder. In particular when straw is used as the vegetable raw material for the process of the invention, a fodder is obtained consisting largely of cellulose and lignin and which is digested by cattle to the extent of about 60 to 70wt.%. To increase the digestibility in particular of wood fibre, it can be subjected in the wet, alkaline condition, e.g. immediately after washing with dilute caustic soda, to treatment with oxygen under pressure. In this known process of oxygen bleaching the lignin content is substantially reduced, e.g. with oak from initially about 24 wt.% to about 18wt.% and the digestibility is increased from about 15 wt.% to about 32 wt.%. For comparison, the digestibility of hay by ruminants is about 55 to 60 wt.%.

Another form in which the process according to the invention can be operated is to subject the fibrinous residue obtained, which consists predominantly of cellulose, to acid or enzymatic hydrolysis to produce glucose. This process is described in detail in Austrian patent application 5345/76 of 20th July 1976.

Since the fibrinous residue obtained according to the invention has an extremely high degree of purity, i.e. the carbohydrate content is mainly cellulose, the hydrolysis produces almost only glucose in excellent yield. It is particularly surprising that the fibrinous residue obtained according to the invention, in spite of the high lignin content, can be degraded enzymatically to glucose in high yield, while wood cannot be enzymatically converted into sugar. Enzymes which degrade cellulose to produce glucose are themselves known. These products are suitable for use in the invention. Processing of the hydrolysis solution to produce glucose can be carried out in a known way.

A substantial technical advance of the process of the invention is that no environmentally harmful chemicals are used and that the chemicals which are used are used in very low concentration. Likewise on environmental grounds, the preferred bleaching with oxygen described above is advantageous.

In the description and in the examples, percentages refer to wt.% unless otherwise stated. The production or isolation and purification of the required material present in solution is carried out by the processes conventional in the field of sugar chemistry, e.g. evaporating down of solutions, addition of liquids in which the required product is insoluble or only slightly soluble, recrystallisation etc.

The following non-limitative Examples illustrate the invention.

EXAMPLE 1—DISINTEGRATION PROCESS 400 g of red beech in the form of hogged chips, air dried, were treated in the laboratory refiner of the firm Defibrator AG with steam for 6 to 7 minutes at 185° to 190° C., corresponding to a pressure of about 12 atm. and defibrated for about 40 sec. The wet fibrinous material obtained was flushed out of the defibrator with a total of 4 l of water and washed on a sieve. The yield of fibrinous material was 83%, calculated on the wood used (absolutely dry).

The washed and pressed fibrinous material was then suspended in 5 l of 1% aqueous NaOH at room temperature and after 30 minutes was separated from the alkaline extract by filtration and pressing. After washing with water, dilute acid and again with water, the yield of fibrinous material was 66%, calculated on the wood used (absolutely dry).

In a corresponding manner, other types of wood, also in the form of coarse sawdust, as well as chopped straw were treated. The mean values of the yields of fibrinous material, calculated on the starting material (absolutely dry) were

| Starting material | Fibrinous residue (%) | |
|---|---|---|
| | After washing with $H_2O$ | After treatment with NaOH |
| Red beech | 83 | 66 |
| Poplar | 87 | 71 |
| Birch | 86 | 68 |

| | Fibrinous residue (%) | |
|---|---|---|
| Starting material | After washing with H₂O | After treatment with NaOH |
| Oak | 82 | 66 |
| Eucalyptus | 85 | 71 |
| Wheat straw | 90 | 67 |
| Barley straw | 82 | 65 |
| Oat straw | 88 | 68 |

EXAMPLE 2—OXYGEN BLEACHING OF FIBRINOUS MATERIAL 280 g of fibrinous material from oak, produced as in Example 1, treated with alkali but not washed with water, equivalent to a quantity of 63 g of absolutely dry fibrinous material was autoclaved under oxygen for one hour up to 120° C. and at 6 atmospheres pressure. At the end of the reaction the material was washed with water, dilute acid and again with water. The remaining fibrinous residue was 82%, calculated on the weight of the fibrinous material used (absolutely dry), or 54% calculated on the wood used in Example 1 (absolutely dry). The lignin content, determined according to TAPPI standard T 13 m-54, was reduced from 24% of the wood originally used to 18%, calculated on the bleached fibrinous material (absolutely dry).

EXAMPLE 3—CARBOHYDRATE COMPOSITION OF FIBRINOUS MATERIALS

The determination of the carbohydrate composition of starting materials and fibrinous materials was carried out after total hydrolysis by quantitative sugar analysis in the Biotronic-Autoanalyser (cf. M. Sinner, M. H. Simatupang and H. H. Dietrichs, *Wood Science and Technology* 9 (1975), p. 307–322).

| | Sugar fraction %, calculated on total carbohydrate fraction. | |
|---|---|---|
| Starting material | Glucose | Xylose |
| Beech | 62 | 31 |
| Fibrin, after washing with water | 75 | 21 |
| Fibrin, after treatment with NaOH | 82 | 15 |
| Oak | 67 | 29 |
| Fibrin, after washing with water | 81 | 17 |
| Fibrin, after treatment with NaOH | 89 | 9 |
| Eucalyptus wood | 74 | 22 |
| Fibrin, after washing with water | 86 | 12 |
| Fibrin, after treatment with NaOH | 93 | 5 |

EXAMPLE 4—DIGESTIBILITY OF THE FIBRINOUS MATERIAL BY RUMINANTS

Portions of about 3 g, accurately weighed, of the air dried (moisture content determined) of the fibrinous material obtained according to Examples 1 and 2 were sewn into polyester net fabric bags and introduced for 48 hours into the stomach of fistulated cattle. The bags with their contents were subsequently carefully washed and dried. The decomposition value in the stomach (digestibility) was determined by reweighing.

| | Decomposition in stomach = digestibility (%) |
|---|---|
| Fibrin washed with water | |
| Wheat | 44 |
| Barley | 55 |
| Oats | 58 |
| Oak | 26 |
| Beech | 22 |
| Poplar | 37 |
| Birch | 16 |
| Eucalyptus | 17 |
| Fibrin treated with 1% NaOH | Digestibility (%) |
| Wheat | 68 |
| Barley | 70 |
| Oats | 66 |
| Oak | 15 |
| Beech | 11 |
| Birch | 20 |
| Oak treated with 1% NaOH + O₂ | 32 |

EXAMPLE 5—MANUFACTURE OF FIBRE BOARDS

The starting material was the red beech and wheat straw fibrinous material described in Example 1, treated with 1% NaOH and washed.

The grinding was carried out in the refiner, first stage at mark 15, second stage at mark 5, with the addition of 0.5% paraffin wax. The fibre mats were formed in the beaten stuff tester at a material consistency of 1.5%.

Cold press: total force 4.7 tonnes for 15 sec.
Hot press:
stage 1 = 23 kg/cm² for 0.5 min.
stage 2 = 3.9 kg/cm² for 3 min.
stage 3 = 14 kg/cm² for 6 min.

Properties, referred to the air dried boards:

| | Thickness mm | Gross density g/cm³ | Bending strength kg/cm² |
|---|---|---|---|
| Beech wood | 2.90 | 1.02 | 709 |
| Wheat straw | 2.73 | 0.99 | 598 |

EXAMPLE 6—CARBOHYDRATE COMPOSITION OF THE AQUEOUS AND ALKALINE EXTRACTS

Figure 1:
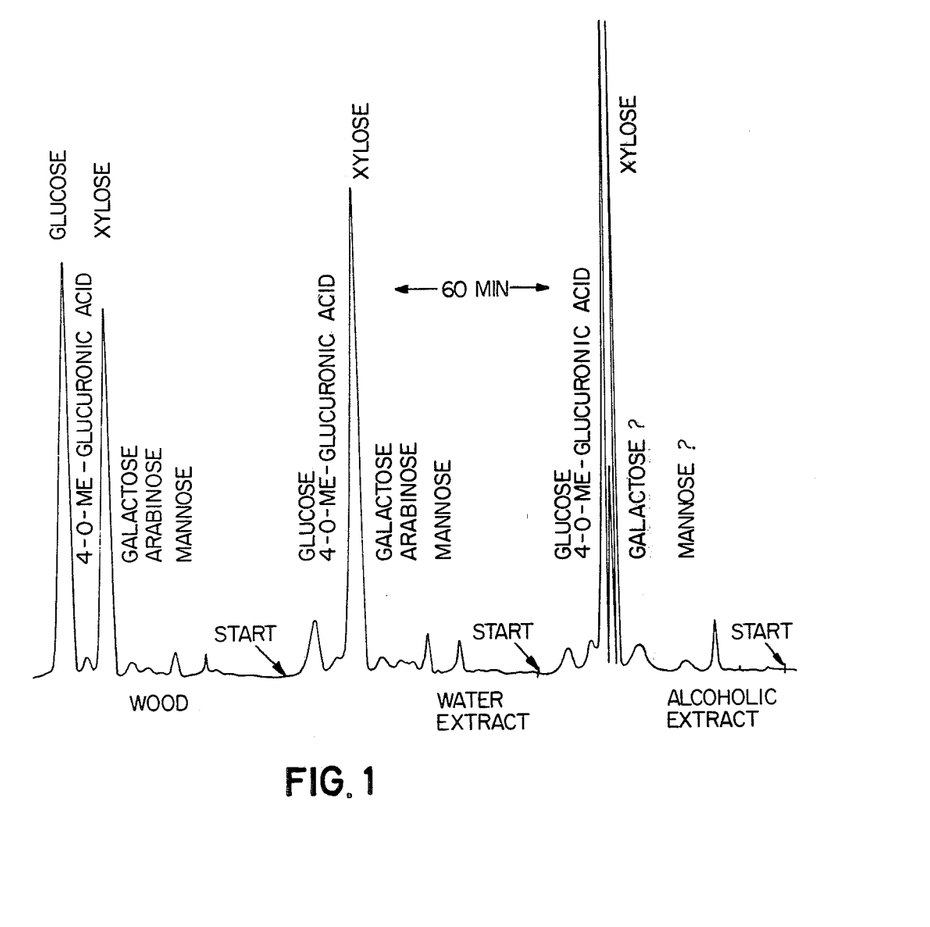

Aliquote parts of the aqueous and alkaline extracts obtained in Example 1 were subjected to total hydrolysis. Individual and total sugars were determined by means of the Biotronic Autoanalyser (cf. Example 3). Wood subjected to total hydrolysis was also examined in the Autoanalyzer. FIG. 1 shows the diagram obtained for red beech.

| | | Dissolved carbohydrates (minimum values) | | |
|---|---|---|---|---|
| | | Total (% on starting material, abs. dry) | Fraction (% calc. on extract) | |
| Extract | | | xylose | glucose |
| Red beech | H₂O | 13.5 | 69 | 13 |
| | NaOH | 7.0 | 83 | 3 |
| Oak | H₂O | 13.2 | 65 | 11 |
| | NaOH | 6.8 | 81 | 5 |
| Birch | H₂O | 11.2 | 77 | 8 |
| | NaOH | 7.3 | 84 | 3 |
| Poplar | H₂O | 8.3 | 76 | 6 |
| | NaOH | 6.5 | 83 | 3 |
| Eucalyptus | H₂O | 9.5 | 71 | 8 |
| | NaOH | 5.0 | 80 | 3 |
| Wheat | H₂O | 7.0 | 53 | 21 |
| | NaOH | 8.3 | 88 | 3 |

-continued

| Extract | | Dissolved carbohydrates (minimum values) | | |
|---|---|---|---|---|
| | | Total (% on starting material, abs. dry) | Fraction (% calc. on extract) | |
| | | | xylose | glucose |
| Barley | H₂O | 6.1 | 41 | 25 |
| | NaOH | 9.5 | 88 | 3 |
| Oats | H₂O | 5.1 | 44 | 20 |
| | NaOH | 4.4 | 88 | 3 |

EXAMPLE 7—INFLUENCE OF TEMPERATURE AND ALKALI CONCENTRATION ON THE CARBOHYDRATE FRACTIONS OF THE EXTRACTS

The fibrinous materials of birch and wheat straw, washed only with water, were treated as in Example 1 with aqueous NaOH at various temperatures and concentrations. The individual and total sugars were determined in the extracts as in Example 6.

| | BIRCH | | |
|---|---|---|---|
| | Dissolved carbohydrates | | |
| | Total (% of starting material | Fractions (% of extract) | |
| Extract | abs. dry | Xylose | Glucose |
| 1% NaOH Room temp. | 7.3 | 84 | 3 |
| 58° C. | 6.3 | 77 | <3 |
| 78° C. | 4.3 | 74 | <3 |
| 0.5% NaOH Room temp. | 9.1 | 91 | 2 |
| 100° C. | 3.3 | 77 | 3 |
| 0.2% NaOH Room temp. | 4.8 | 84 | 3 |
| 100° C. | 3.8 | 82 | 3. |
| WHEAT STRAW. | | | |
| | Dissolved carbohydrates | | |
| | Total % of starting material | Fractions (% of extract) | |
| Extracts with 1% NaOH | abs. dry | Xylose | Glucose |
| Room temp. | 7.1 | 81 | 4 |
| 56° C. | 9.5 | 79 | 5 |
| 63° C. | 9.9 | 79 | 5 |
| 80° C. | 7.9 | 77 | 4 |

EXAMPLE 8—TEMPERATURE STABILITY OF THE XYLOSE CONTENT OF ALKALINE EXTRACTS

Aliquote fractions of the alkaline extracts of birch obtained as in Example 1 were warmed for 30 minutes in a water bath to temperatures between 25° and 100° C. After this treatment they were subjected to total hydrolysis and the sugar composition was quantitatively determined by means of the Biotronic Autoanalyser (cf. Example 3). It was demonstrated that the warming treatment to about 75° C. did not alter the content of xylose and other sugars in the solutions. Above 75°–80° C. the xylose content of the solutions decreased with warming at increasingly high temperatures.

EXAMPLE 9—ISOLATION OF XYLAN FROM THE ALKALI EXTRACT

The alkali extract obtained in Example 1 from 400 g of air dried barley straw was acidified to pH 5. The precipitate produced=5.6%, calc. on the straw used (abs. dry) was separated from the supernatant layer by centrifuging. The hydrolysis residue of the precipitate was 30%. To the clear supernatant liquid=(5 l), methanol (15 l) was added and the white precipitate produced was again separated by centrifuging. The yield was 4.2% calc. on the straw used (abs. dry). The hydrolysis residue of this precipitate was 3.2% and the ash content 2.2%. After total hydrolysis and quantitative sugar analysis as in Example 3, the purified precipitates still contain 3.5% glucose and 1.5% galactose as secondary constituents.

EXAMPLE 10—REMOVAL OF IMPURITIES FROM AQUEOUS EXTRACTS

The aqueous extract from red beech obtained in Example 1 was freed from impurities, in particular organic colouring matter, on a strongly basic macroreticular ion exchanger in the Cl form. For this purpose, for 100 ml of extract, 4 ml Lewatit MP 5080 (Merck AG) was used in a column of 1 cm diameter. The corresponding ion exchanger IRA 900 of Amberlite is equally suitable. After the extract had passed through, the column was washed twice with 4 ml portions of distilled water. The carbohydrate yield of the purified solutions, which were still coloured light yellow by impurities, amounted on average to about 95% of the quantity taken.

EXAMPLE 11—SEPARATION OF FREE MONOSACCHARIDES FROM AQUEOUS EXTRACTS BY EVAPORATION AND ELUTION OF THE XYLANS AND XYLAN FRAGMENTS WITH SALT OR ACID 16 ml of the aqueous extract obtained from red beech in Example 1 were applied to 5 ml Lewatit MP 5080 (Merck AG) in the OH form (column diam. 1.1 cm). The column was flushed with about 30 ml of distilled water. This solution contained on average 5% of the quantity of carbohydrate applied, comprising, arranged in order of quantity, arabinose (30%), xylose (22%), glucose (17% including fructose, which can be produced on the ion exchanger by conversion from glucose), galactose (12%) and rhamnose (10%). The first fractions of the column eluate contained substantially more glucose and fructose (up to 50%) and only small amounts of xylose. Subsequently the proportion of xylose increased. If the ion exchanger is overloaded, or in the case of elution with caustic soda the alkali solution is too strong or too much is used, increased amounts of xylose and subsequently xylobiose and neutral xylo-oligomers are washed down from the ion exchanger.

Subsequently, the xylans and xylan fragments were washed down with 2% soda solution. The first 40 ml contained on average 85% of the quantity of carbohydrate applied. The hydrolysate of these solutions contained on average 84% xylose and, in addition to the 4-O-methylglycuronic acid originating from the xylan, only glucose as foreign sugar (average 8%).

When xylans and xylan fragments were washed out of the ion exchanger with 2% phosphoric acid, more liquid (about 60 ml) was needed and the yield was lower. On average about 75% of the quantity of carbohydrate was recovered (including monosaccharides).

EXAMPLE 12—HYDROLYSIS OF THE XYLANS AND XYLAN FRAGMENTS IN THE ION EXCHANGE BED 18 ml of the extract from red beech obtained in Example 1, purified on Lewatit MP 5080 in Cl form, as described in Example 10, treated on 5 ml of Lewatit MP 5080 in OH form to remove monosaccharides as described in Example 11.

After expression of the water with compressed air, 4 ml of 10% sulphuric acid (note high acid concentration, but small quantity of liquid) was added to the ion exchanger, which was then stoppered and heated for 1 hour in a boiling water bath. The acid was then expressed and the ion exchanger was rinsed with 2 ml of distilled water. The solution contained about 75% of the quantity of carbohydrate taken and therefore had a concentration of about 3%. A further 7 ml of wash water contained 8% and the next 9 ml of water 0.5% of the quantity of carbohydrate taken. The purified sulphuric acid hydrolysate showed the same purity as the xylans and xylan fragments eluted with soda or phosphoric acid and subsequently hydrolysed (cf. Example 11).

Overall in this experiment about 90% of the carbohydrate taken was recovered. Similar results were obtained by hydrolysis of the xylans and xylan fragments in the ion exchange bed with 20 ml of 2% nitric acid.

EXAMPLE 13—COMPARATIVE ACID HYDROLYSIS OF XYLAN EXTRACTS AND WOOD

To 20 ml of the aqueous extract from red beech produced in Example 1, 340 mg. of xylan, obtained according to Example 9 from alkaline red beech extracts, and conc. $H_2SO_4$ were added, so that the solution contained about 3% xylan and 0.5% $H_2SO_4$. The solution was heated in a stoppered flask in the boiling water bath and the course of the hydrolysis was followed reductiometrically (cf. M Sinner and H. H. Dietrichs, Holzforschung 30 (1976), 50–59). As a comparative experiment, 1,8 g of beech chips (sieve fraction 0.1 to 0.3 mm) were treated in the same way in 20 ml of 0.5% aqueous $H_2SO_4$.

The xylan obtained according to the invention was hydrolysed to more than 50% after 30 min. and completely after 3 hours. From the wood, which was known to contain about 28% xylan, there was liberated after 30 minutes 3%, after 3 hours 8% and after 9 hours 10% of reducing sugar, largely xylose.

EXAMPLE 14—ACID HYDROLYSIS OF FIBRINOUS MATERIAL 300 mg portions of the fibrins of oak and eucalyptus obtained as in Example 1, treated with alkali, were, in the usual way for total hydrolysis (cf. J. F. Saeman, W. E. Moore, R. L. Mitchell and M. A. Millet, Tappi 37 (1954), 336–343) mixed with 3 ml of conc. $H_2SO_4$ with cooling, incubated for 60 min. at 30° C., diluted with 84 ml water and heated for 120° C. for 60 min.

Figure 2:
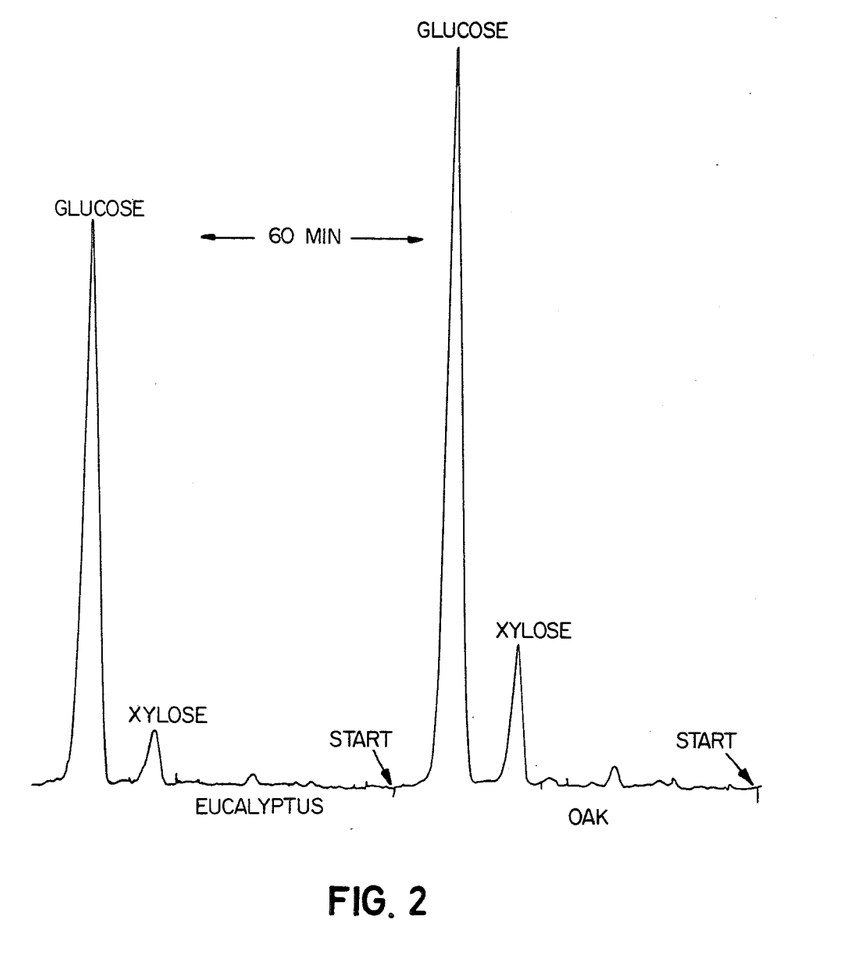

After this treatment, the solutions contained, calculated on the fibrinous material weighed out, about 70% monosaccharides. Quantitative sugar analysis of the solutions (cf. Example 3) gave for oak a glucose proportion of 89% and for eucalyptus 93%. FIG. 2 shows on the right the sugar chromatogram of the fibrin hydrolysate of oak and on the left that of eucalyptus.

EXAMPLE 15—ENZYMATIC HYDROLYSIS OF FIBRINOUS MATERIAL

Starting materials were the fibrinous residues of oak obtained according to Example 1 by treatment with 1% NaOH and washing and the fibrinous residue of birch obtained according to Example 7 by treatment with 0.5% NaOH at room temperature and washing after drying in the conditioning room (mean residual moisture 10 wt.%)

200 mg of these fibrinous residues were incubated in 5 ml of 0.1 m sodium acetate buffer pH 4.8 at 46° C. in a shaker water bath with 25 mg of a product obtained by dialysis and subsequent freeze drying from the commercial enzyme preparation Onozuka SS (All Japan Biochemicals Co., Nishinomiya, Japan). Thimerosal (28 mg/l) was added to the solutions to inhibit growth of microorganisms. Two samples of each were incubated with enzyme and 1 sample without enzyme (control). The decomposition was followed by quantitative sugar analysis (cf. Example 3). After 24 hours incubation the remaining residue was separated by suction through a sintered filter (G3), dried and weighed. The end decomposition was additionally measured by determination of the amount of carbohydrate which had passed into solution (in the filtrate) with orcinol-sulphuric acid (cf. M. Sinner, N. Parameswaran, H. H. Dietrichs and W. Liese, Holzforschung 27 (1973), 36–42).

Figure 3:
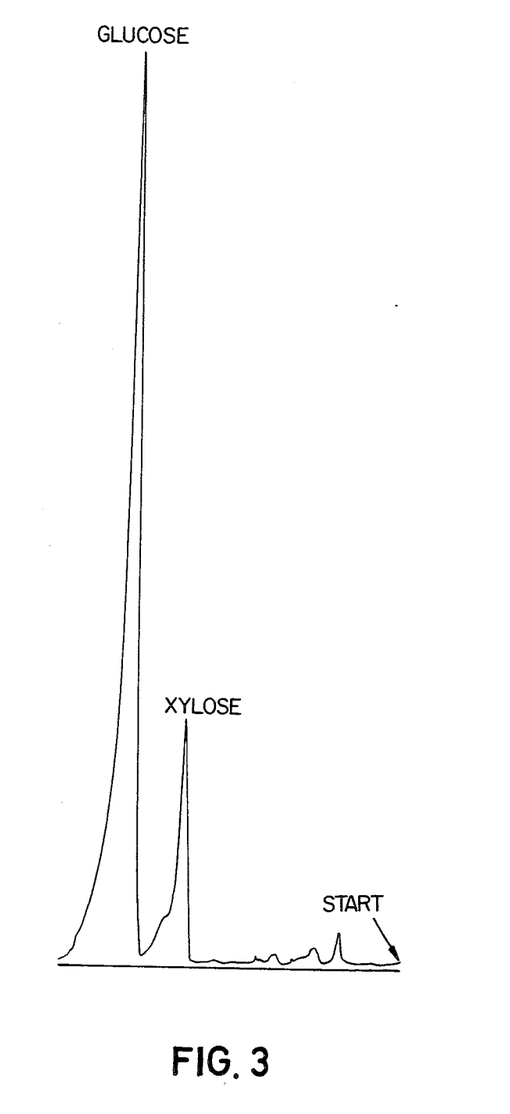

After an incubation period of 2.25 hours, the oak fibrin had been converted on average 17% into monomeric and oligomeric sugars; the corresponding value for birch was 18%. The end decomposition value for oak mounted on average to 24% and for birch an average of 42%. The sugar chromatograms of the end decomposition solutions contained only monosaccharides, viz. glucose and xylose. The ratio of glucose to xylose corresponded approximately to that reached in acid hydrolysis. In the enzymatic degraded oak fibrin the glucose fraction was 84% and in the birch fibrin 81%. FIG. 3 is the sugar chromatogram of the end decomposition solution of oak. It is similar to the chromatogram of the sulphuric acid oak fibrin hydrolysate of Example 14 (FIG. 2).

Taking into account the lignin content of the fibrin of 22 to 24%, it is found that the carbohydrate, which consists mainly of cellulose (cf. Example 3), can be converted into sugar to the extent of about 54%, mainly into glucose.

What is claimed is:

1. A process for the production of xylan and fibrinous material from xylan-containing vegetable raw material which can be disintegrated by steam pressure treatment and defibration comprising the steps of
   (a) treating the raw material with saturated steam under pressure at a temperature of from about 175°–220° C. for a period of two minutes to four hours,
   (b) lixiviating the treated vegetable raw material with aqueous solution whereby xylan and xylan fragments are extracted from the disintegrated raw material producing an aqueous xylan extract solution and a fibrinous residue.

2. The process according to claim 1, wherein the xylan and xylan fragments in the extract solution are hydrolized by treatment with hydrolyzing agents to produce xylose.

3. The process according to claim 2, wherein the xylose is reduced by catalytic hydrogenation to obtain xylitol.

4. The process according to claim 1 wherein the fibrinous residue obtained after lixiviation of the disintegrated vegetable raw material is washed with water to obtain a fibrinous material.

5. The process according to claim 1, wherein the vegetable fibrinous residue is bleached with oxygen.

6. The process according to claim 1, wherein the fibrinous residue obtained is subjected to hydrolysis to produce glucose.

7. The process of claim 1 wherein the lixiviation is effected in an alkaline solution containing from about 0.1 to 4% by weight of sodium hydroxide.

8. The process of claim 1 wherein the xylan extract solution is purified by treatment with a strongly basic ion exchange resin in the OH form.

9. The process of claim 8 wherein the xylose is recovered in crystalline form.

10. The process of claim 1 wherein the fibrinous residue produced in step (b) is lixiviated with a dilute alkaline solution forming a fibrinous residue and a second xylan extract solution.

* * * * *

UNITED STATES PATENT AND TRADEMARK OFFICE
CERTIFICATE OF CORRECTION

PATENT NO. : 4,181,796
DATED : January 1, 1980
INVENTOR(S) : Hans-Hermann Dietrichs, et al It is certified that error appears in the above—identified patent and that said Letters Patent is hereby corrected as shown below:

IN THE TITLE: delete "FIBRIN" and insert --FIBER--.

IN THE ABSTRACT: line 1, delete "fibrinous" and insert --fiber--.

IN THE DRAWINGS: FIG. 1, delete "ALCOHOLIC EXTRACT" and insert --ALKALINE EXTRACT--.

Column 1, line 7, delete "fibrin" and insert --fiber--;
        line 19, delete "defibrination" and insert --defibration--;
        line 30, delete "defibrination" and insert --defibration--;
        line 45, delete "fibrinous" and insert --fiber--.

Column 2, line 5, delete "defibrination" and insert --defibration--;
        line 48, delete "defibrination" and insert --defibration.

Column 4, line 61, delete "fibrins" and insert --fibers--.

Column 7, line 32, first and second occurrences, delete "fibrinous" and insert --fibrous--;
        line 37, delete "fibrinous" and insert --fibrous--;
        line 44, delete "fibrinous" and insert --fibrous--;
        line 50, delete "fibrinous" and insert --fibrous--.

UNITED STATES PATENT AND TRADEMARK OFFICE
CERTIFICATE OF CORRECTION

PATENT NO. : 4,181,796

DATED : January 1, 1980

INVENTOR(S) : Hans-Hermann Dietrichs, et al

It is certified that error appears in the above—identified patent and that said Letters Patent is hereby corrected as shown below:

```
Column 8, line  4, delete "fibrinous" and insert --fibrous--;
         line  9, delete "fibrinous" and insert --fibrous--;
         line 13, delete "fibrinous" and insert --fibrous--;
         line 45, delete "fibrinous" and insert --fiber--;
         line 48, delete "fibrinous" and insert --fiber--;
         line 55, delete "fibrinous" and insert --fiber--;
         line 59, delete "fibrinous" and insert --fiber--;
         line 63, delete "Fibrinous" and insert --Fibrous--.

Column 9, line  2, delete "Fibrinous" and insert --Fibrous--;
         line 14, delete "FIBRINOUS" and inser --FIBER--;
         line 15, delete "fibrinous" and insert --fiber--;
         line 18, delete "fibrinous" and insert --fiber--;
                  delete "fibrinous" bridging lines 21
         and 22, and insert --fibrous--;
         line 23, delete "fibrinous" and insert --fiber--;
         line 28, delete "fibrinous" and insert --fiber--;
         line 31, delete "FIBRINOUS" and insert --FIBER--;
         line 34, delete "fibrinous" and insert --fiber--;
         line 44, delete "Fibrin" and insert --Fiber--;
         line 46, delete "Fibrin" and insert --Fiber--;
         line 49, delete "Fibrin" and insert --Fiber--;
         line 51, delete "Fibrin" and insert --Fiber--;
         line 54, delete "Fibrin" and insert --Fiber--;
         line 56, delete "Fibrin" and insert --Fiber--;
         line 59, delete "FIBRINOUS" and insert --FIBER--;
         line 62, delete "fibrinous" and insert --fiber--.
```

UNITED STATES PATENT AND TRADEMARK OFFICE
CERTIFICATE OF CORRECTION

PATENT NO. : 4,181,796

DATED : January 1, 1980

INVENTOR(S) : Hans-Hermann Dietrichs, et al

It is certified that error appears in the above—identified patent and that said Letters Patent is hereby corrected as shown below:

```
Column 10, line  3, delete "Fibrin" and insert --Fiber--;
           line 11, delete "Fibrin" and insert --Fiber--;
           line 23, delete "fibrinous" and insert --fiber--.

Column 11, line 17, delete "fibrinous" and insert --fiber--.

Column 12, line 28, delete "EVAPORATION" and insert
--DISPLACEMENT--.

Column 13, line 45, delete "FIBRINOUS" and insert --FIBER--;
           line 47, delete "fibrins" and insert --fibers--;
           line 55, delete "fibrinous" and insert --fiber--;
           line 59, delete "fibrin" and insert --fiber--;
           line 63, delete "FIBRINOUS" and insert --FIBER--;
           line 64, delete "fibrinous" and insert --fibrous--;
           line 66, delete "fibrinous" and insert --fibrous--.

Column 14, line  3, delete "fibrinous" and insert --fibrous--;
           line 22, delete "fibrin" and insert --fiber--;
           line 30, delete "fibrin" and insert --fiber--;
           line 31, delete "fibrin" and insert --fiber--;
           line 34, delete "fibrin" and insert --fiber--;
           line 36, delete "fibrin" and insert --fiber--;
```

UNITED STATES PATENT AND TRADEMARK OFFICE
CERTIFICATE OF CORRECTION

PATENT NO. : 4,181,796

DATED : January 1, 1980

INVENTOR(S) : Hans-Hermann Dietrichs, et al

It is certified that error appears in the above—identified patent and that said Letters Patent is hereby corrected as shown below:

Column 14, line 55, delete "fibrinous" and insert --fibrous--
line 64, delete "fibrinous" and insert --fibrous--
line 66, delete "fibrinous" and insert --fiber--;
line 68, delete "fibrinous" and insert --fibrous--

Column 15, line 2, delete "fibrinous" and insert --fibrous--.

Column 16, line 5, delete "fibrinous" and insert --fibrous--;
line 7, delete "fibrinous" and insert --fibrous--.

Signed and Sealed this

Sixth Day of January 1981

[SEAL]

Attest:

SIDNEY A. DIAMOND

Attesting Officer

Commissioner of Patents and Trademarks